(12) United States Patent
Choate et al.

(10) Patent No.: US 6,308,142 B1
(45) Date of Patent: Oct. 23, 2001

(54) METHOD FOR DETERMINING FLAME RETARDANCE OF POLYMER COMPOSITIONS

(75) Inventors: Kim Choate, Moka (JP); Angela R. Neff, Clifton Park, NY (US); Paul Cletus Raymond III, Tokyo (JP); Patrick A. Rodgers, Selkirk; Ronald James Wroczynski, Schenectady, both of NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/250,052

(22) Filed: Feb. 12, 1999

(51) Int. Cl.[7] ................................................. G06F 101/14
(52) U.S. Cl. .......................... 702/179; 702/181; 252/609; 524/409
(58) Field of Search ....................... 702/179, 180, 702/181; 252/601, 609–611; 524/409, 525

(56) References Cited

U.S. PATENT DOCUMENTS 3,816,367 * 6/1974 Larkin et al. ..................... 252/609
4,080,404 * 3/1978 Deets ................................. 524/409
5,158,999 * 10/1992 Swales et al. ..................... 252/609

FOREIGN PATENT DOCUMENTS

| 27 40 850 A | 3/1979 | (DE) . |
| 0122110 | * 10/1984 | (EP) . |
| 0 855 421 A | 7/1998 | (EP) . |

OTHER PUBLICATIONS

Steven Walter, "Filled polypropylene can be flexible—and flame retardant, too.", Plastics Engineering, USA, vol. 37, No. 6, pp. 24–27 (Jun. 1981).

* cited by examiner

Primary Examiner—Marc S. Hoff
Assistant Examiner—Bryan Bui

(57) ABSTRACT

A method for determining flame retardance of polymer compositions includes subjecting a plurality of specimens of a polymer composition to a flame test and performing a statistical analysis of the data obtained. The statistical analysis includes determining the probability of at least one possible outcome of the flame test. The probability of possible outcomes provides a measure of the flame retardance of the polymer composition. A preferred flame test is the UL-94 flame test.

30 Claims, 3 Drawing Sheets

METHOD FOR DETERMINING FLAME RETARDANCE OF POLYMER COMPOSITIONS
Choate, et al
09/250,052
08CN08794

METHOD FOR DETERMINING FLAME RETARDANCE OF POLYMER COMPOSITIONS

FIELD OF THE INVENTION

The invention relates to methods for the determination of flame retardance of a polymer composition.

BACKGROUND OF THE INVENTION

In many applications where polymers are used, it is necessary that the polymer composition and article fabricated from the polymer composition possess some flame retardance in order to minimize the danger of fire. For example, in electrical appliances, an electrical short can start a fire. The plastic housing, therefore, should be made of a material which does not burn easily.

For most polymer compositions, it is necessary to add materials to the composition that impart flame retardance to the article. Examples of materials which have been used to impart such flame retardance are brominated resins, antimony oxide fillers, and organic phosphates. These materials add significant costs to a polymer composition, and can have a negative impact on other properties, so it is desirable to limit flame retardants to the minimum amount necessary to impart flame retardance to the polymer composition.

Underwriters Laboratories has developed a variety of tests for materials which are to be used with or near electricity, including a flame test. The UL rating is very influential, and has become an industry standard. A polymer composition which does not have a UL flame rating will not be purchased for applications which require flame retardance. Likewise, a polymer composition which loses its UL flame rating will no longer be sold for the applications for which it was designed, those requiring flame retardance. Therefore, it is important that a new flame-retardant polymer composition receive a rating of flame retardant initially, and it is critical that the rating is maintained thereafter.

The Underwriters Laboratories flame test is designated UL-94. Briefly, one of the test protocols calls for exposing five bars of a polymer composition to a flame to initiate burning, removing the flame and recording the time for the flame to go out. The polymer composition tested can receive a rating of V-0 (most flame retardant), V-1, or V-2 (least flame retardant), depending on the results of the test.

Unfortunately, for a test that is vital to the commercial success of many polymer compositions, the UL-94 flame test yields results which can be notoriously variable. That is, there is high statistical variability associated with the results of the test. The variability has been attributed to differences in sample preparation, operator-to-operator variation, and even to changes in the burn mechanism.

Use of results from the UL-94 test to determine the amount of flame retardant to be added can lead to the addition of excessive amounts in order to guarantee compliance with the requirements of the test. Therefore, there is a need for an improved method for the determination of flame retardance of polymer compositions. In particular, there is a need for less variable, more quantifiable method of determining the performance of a polymer composition in the UL-94 test without changing the UL-94 test protocol.

SUMMARY OF THE INVENTION

The present invention provides a method for determining flame retardance of polymer compositions which overcomes the problem of the variability of the results of the UL-94 test. The method includes subjecting a plurality of specimens of a polymer composition to a flame test and performing a statistical analysis of the data obtained. The statistical analysis includes using the data to determine a probability of at least one possible outcome of the flame test, wherein the probability of the outcome provides a measure of the flame retardance of the polymer composition.

In one aspect, the flame test is a UL-94 flame test. In another aspect, at least twenty specimens are tested.

In one embodiment, possible outcomes are a first time pass, a retest, a first submittal pass, a second submittal pass, and a failure.

One possible outcome is a first time pass. The probability of a first time pass is determined according to:

$$P_{first\ time\ pass} = (P_{t1>mbt,\ n=0} \times P_{t2>mbt,\ n=0} \times P_{total<=mtbt} \times P_{drip,\ n=0})$$

where $P_{t1>mbt,\ n=0}$ is a probability that no first burn time exceeds a maximum burn time value, $P_{t2>mbt,\ n=0}$ is a probability that no second burn time exceeds a maximum burn time value, $P_{total<=mtbt}$ is a probability that a sum of the burn times is less than or equal to a maximum total burn time value, and $P_{drip,\ n=0}$ is a probability that no specimen of the plurality of specimens exhibits dripping during the flame test.

Another possible outcome is a retest. The probability of a retest is determined according to:

$$P_{retest} = (P_{t1>mbt,\ n=1} \times P_{t2>mbt,\ n=0} \times P_{total<=mtbt} \times P_{drip,\ n=0})$$
$$+ (P_{t1>mbt,\ n=0} \times P_{t2>mbt,\ n=1} \times P_{total<=mtbt} \times P_{drip,\ n=0})$$
$$+ (P_{t1>mbt,\ n=0} \times P_{t2>mbt,\ n=0} \times P_{mtbt<total<=mrtbt} \times P_{drip,\ n=0})$$
$$+ (P_{t1>mbt,\ n=0} \times P_{t2>mbt,\ n=0} \times P_{total<=mtbt} \times P_{drip,\ n=1})$$

where $P_{t1>mbt,\ n=1}$ is the probability that a single first burn time exceeds a maximum burn time value, $P_{t2>mbt,\ n=1}$ is the probability that a single second burn time exceeds a maximum burn time value, $P_{mtbt<total<=mrtbt}$ is the probability that the sum of individual burn times is greater than the maximum total burn time value and is less than or equal to the maximum retest total burn time value and $P_{drip,\ n=1}$ is the probability that a single specimen exhibits dripping during the flame test and $P_{t1>mbt,\ n=0}$, $P_{t2>mbt,\ n=0}$, $P_{total<=mtbt}$, and $P_{drip,\ n=0}$, are as defined above.

Still another possible outcome is a failure. The probability of a failure is determined according to:

$$P_{failure,\ no\ retest} = 1 - P_{first\ time\ pass} - P_{retest}$$

Another possible outcome is a first submittal pass. The probability of a first submittal pass is determined according to:

$$P_{1st\ submittal\ pass} = P_{first\ time\ pass} + P_{retest} \times P_{first\ time\ pass}$$

Another possible outcome is a second submittal pass. The probability of a second submittal pass is determined according to:

$$P_{2nd\ submittal\ pass} = P_{failure,\ no\ retest} \times (P_{first\ time\ pass} + P_{retest} \times P_{first\ time\ pass})$$

where $P_{first\ time\ pass}$ is the probability of a first time pass and $P_{retest}$ is the probability of a retest and $P_{failure}$, no retest is the probability of a failure.

In another aspect of the invention, a system for determining flame retardance of a polymer composition is provided. The system includes means for obtaining data resulting from subjecting a plurality of specimens of a polymer composition to a flame test, and means for performing statistical analysis of the data. The means for performing statistical analysis includes means for using the data to determine a probability of at least one possible outcome of the flame test. The probability of the possible outcome provides a measure of the flame retardance of the polymer composition.

In yet another aspect of the present invention, an article of manufacture is provided. The article of manufacture includes a computer usable medium having computer readable program code means embodied therein for causing the determining of flame retardance of polymer compositions. The computer readable program code means in the article of manufacture includes a first computer readable program code segment for causing a computer to obtain data resulting from subjecting a plurality of specimens of a polymer composition to a flame test; and a second computer readable program code segment for causing a computer to perform a statistical analysis of the data. The statistical analysis includes using the data to determine a probability of at least one possible outcome of the flame test. The probability of the possible outcome provides a measure of the flame retardance of the polymer composition.

DETAILED DESCRIPTION OF THE INVENTION

The present invention provides a method for the determination of the flame retardance of a polymer composition. In particular, a plurality of specimens of a polymer composition may be subjected to a flame test and the data obtained therefrom analyzed to yield a measure of the flame retardance of the polymer composition.

According to the method of the present invention, a plurality of specimens of a polymer composition may be subjected to flame testing. While Underwriters Laboratories mandates the testing of as few as five specimens, it has been discovered that testing at least twenty specimens initially provides a superior measure of the flame retardance of a polymer composition. Therefore, it is preferred that at least twenty specimens be tested. A greater number of specimens may be tested if desired. In general, testing a larger number of specimens provides smaller confidence intervals for the analysis.

The specimens may be prepared by methods well known in the art. For example, specimens of thermoplastic resins are typically ls prepared by injection molding. Any method which can produce a bar of the required standard dimensions may be used, including milling a larger piece to the desired size.

In one embodiment of the invention, the flame test employed is the UL-94 flame test. This flame test is preferred as it is a current industry standard. However, other flame tests providing similar results, in particular, burn times, may also be used. The UL-94 test is particularly suitable for thermoplastic polymers and may be used for other types of polymers. Other tests may be utilized for other types of polymers, if desired.

Figure 1:
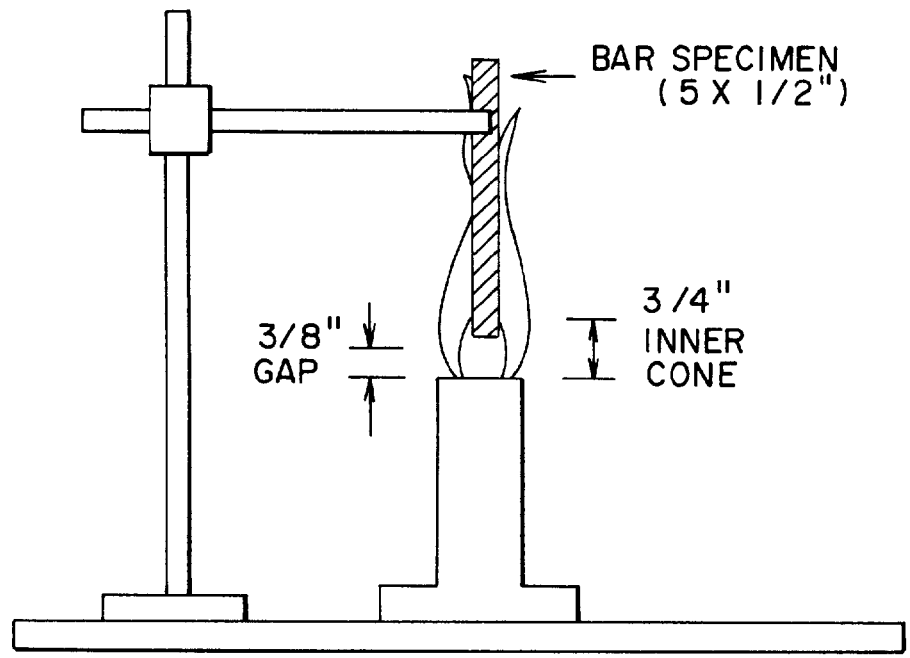
FIG. 1 is a diagram of the Underwriters Laboratories UL-94 test protocol.

The physical layout of the UL-94 test is illustrated in FIG. 1. The protocol calls for bar-shaped specimens of dimensions 5"(12.7 cm)×½" (1.3 cm) width×the desired normal thickness, UL-94 ratings being specified for a particular thickness. A flame having an inner cone of height ¾" (1.9 cm) is applied to each specimen so that a distance of ⅜" (1.0 cm) separates the lower end of the specimen from base of the flame. The flame is held in that position for 10 seconds and then removed. A burn time is defined as the time required for the flame issuing from the specimen to disappear. If burning of the specimen ceases within 30 seconds, the flame is reapplied for an additional 10 seconds. The criteria for V-0, V-1, and V-2 ratings are listed in Table 1.

TABLE 1

Vertical Flame Class Requirements

|  | 94V-0 | 94V-1 | 94V-2 |
| --- | --- | --- | --- |
| Individual burn time, seconds | #10 | #30 | #30 |
| Total burn time, s (5 specimens × 2) | #50 | #250 | #250 |
| Glowing time, s (individual specimen) | #30 | #60 | #60 |
| Drip particles that ignite cotton | NO | NO | YES |

For a V-0 rating, no individual burn times, from the first or second application may exceed 10 seconds. The total of the burn times for any five specimens may not exceed 50 seconds. Drip particles that ignite a piece of cotton gauze situated below the specimen are not allowed.

For a V-1 rating, no individual burn times, from the first or second application may exceed 30 seconds. The total of the burn times for any five specimens may not exceed 250 seconds. Drip particles that ignite a piece of cotton gauze situated below the specimen are not allowed.

For a V-2 rating, no individual burn times, from the first or second application may exceed 30 seconds. The total of the burn times for any five specimens may not exceed 250 seconds. Drip particles that ignite a piece of cotton gauze situated below the specimen are allowed.

Figure 3:
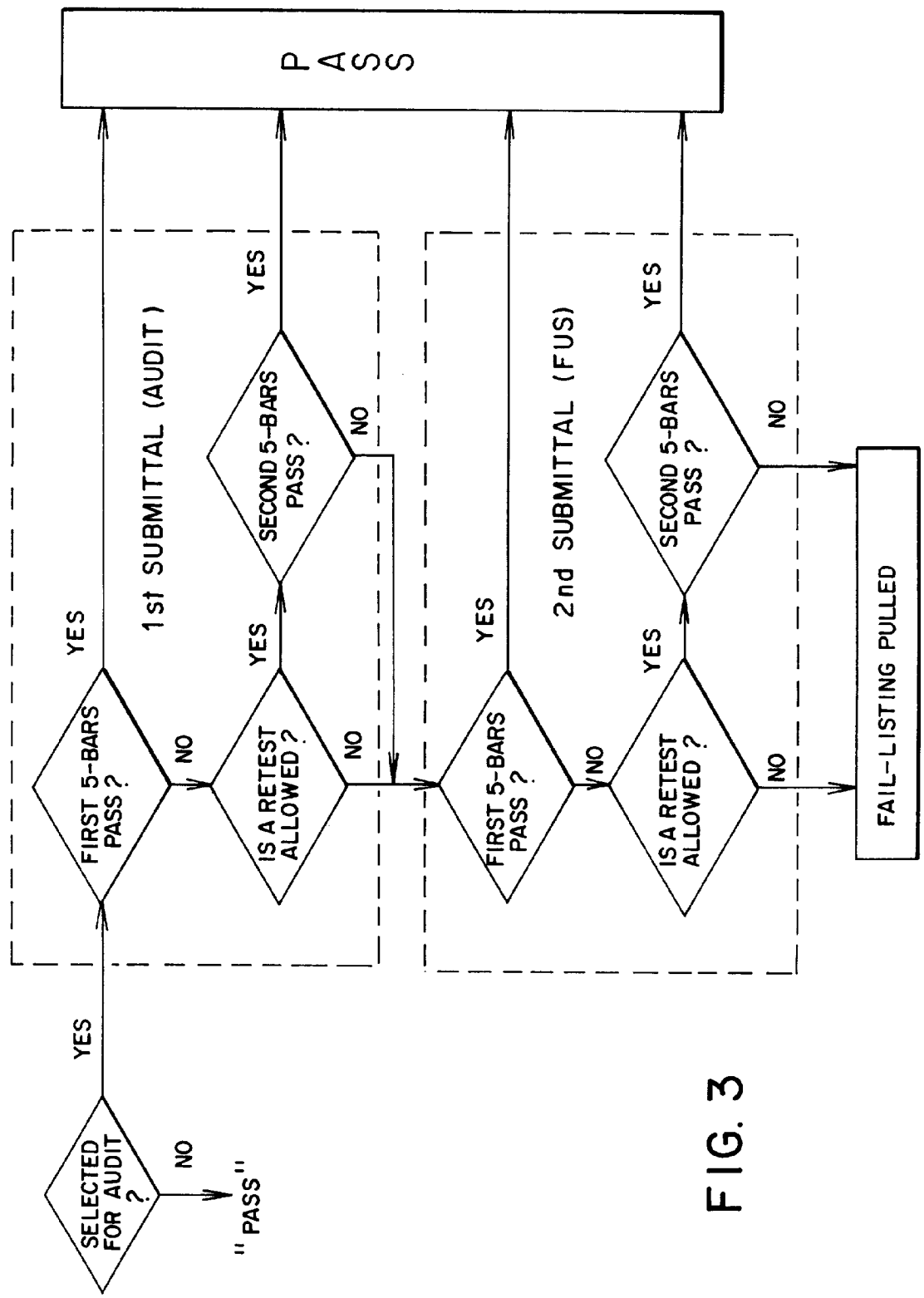
FIG. 3 is a flow chart illustrating the UL Audit/Follow-up Services Process.

Underwriters Laboratories performs a periodic audit of every polymer composition or grade which bears a UL flame rating. A diagram of the UL Audit/Follow-up Services process is shown in FIG. 3. During an audit, five specimens of a polymer composition are tested initially.

A retest of five additional specimens is allowed under certain conditions amounting to a "near miss," that is, a single specimen does not meet a single requirement for a pass rating. Specifically, these conditions are:

a single burn time exceeds the maximum burn time value (V-0, 10 seconds; V-1, V-2, 30 seconds); or a sum of individual burn times is greater than the maximum total burn time allowed (V-0, 50 seconds; V-1, V-2 250 seconds) and is less than or equal to the maximum retest total burn time value (V-0, 55 seconds, V-1, V-2, 255 seconds); or a single specimen exhibits dripping during the test.

Where a single specimen of a polymer composition fails to meet any one of these conditions, a retest of a second set of specimens is allowed. The polymer composition may pass the flame test on a retest; the requirements listed in Table 1 are applied to retest data. If a single specimen or the set of specimens fails to meet more than one condition, no retest is allowed and a first submittal failure occurs.

Because the consequences of failing an audit are extremely serious, UL Follow-up Services provides for submittal of a second set of samples. On a second submittal, the second set of specimens is tested exactly as a first set. Five specimens are tested initially, with five additional specimens retested if the conditions are met under which a retest is allowed (described above). The polymer composition may pass the flame test on a second submittal, either on testing the initial five specimens or on a retest. The requirements listed in Table 1 are applied to second submittal data.

Therefore, the data obtained from the UL-94 flame test may be in the form of burn times for first and possibly second applications of a flame to a single specimen, for first submission specimens tested initially and retested, and for second submission specimens tested initially and retested. Data relating to dripping of the various specimens may also be considered.

The method of the present invention provides for performing a statistical analysis of the data obtained from a flame test to determine the probability of at least one possible outcome of the test. Possible outcomes include a first submittal pass, including first time pass and retest, and a second submittal pass, including first time pass and retest, and failure. The probability of at least one outcome, preferably a first time pass on a first submission, provides a measure of the flame retardance of the polymer composition, while minimizing the variability inherent in flame testing, particularly the UL-94 test.

Figure 2:
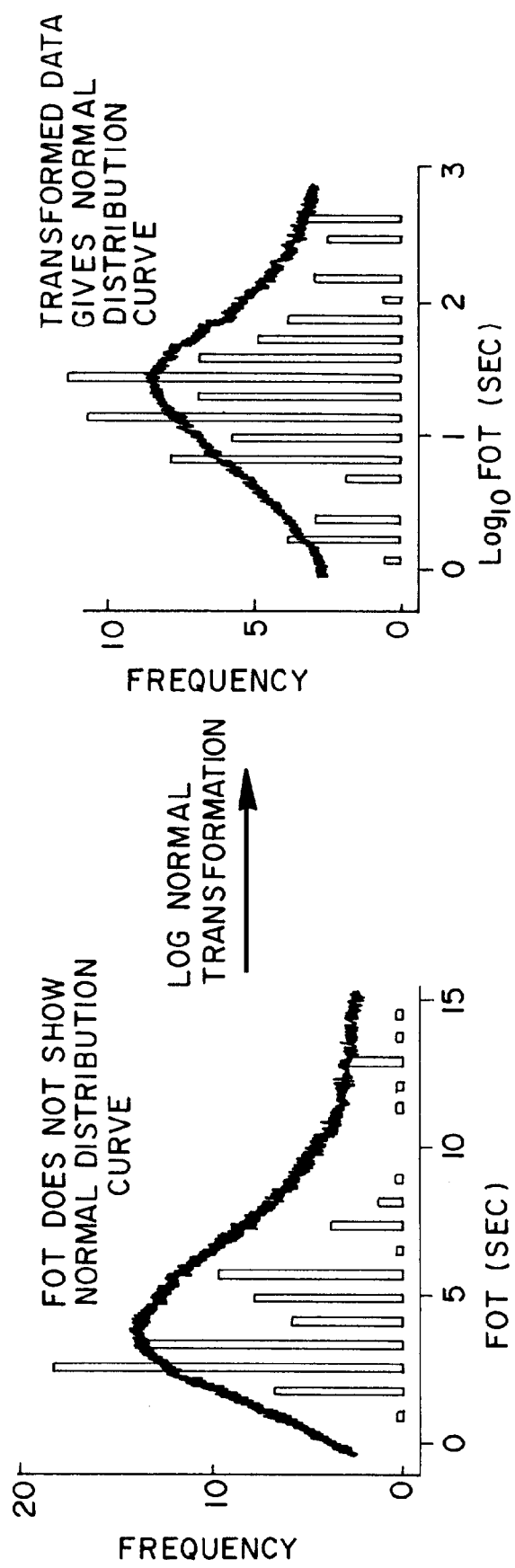
FIG. 2 shows a distribution curve for burn time data obtained from a typical UL-94 flame test, in comparison with a distribution curve for a logarithmic transformation of the data.

The raw data may be transformed prior to use in the statistical calculations by conversion to equivalent logarithmic values. ("Logarithm" and "logarithmic" refer to base 10 logarithms.) Times less than one second may be rounded up to one second in order to avoid negative logarithmic values. The logarithm of the burn time may then be calculated and used in subsequent steps. Use of transformed data is preferred as a more normal distribution of values associated with burn time is thereby provided, as shown in FIG. 2. Raw data do not show a normal (bell-shaped) distribution curve because there can be no values less than zero, and data points are typically clustered in the space below the maximum individual burn time. The transformed data, however, more closely fit a normal distribution curve, as shown in the figure.

The probability of a first time pass may be determined according to the formula:

$$P_{first\ time\ pass} = (P_{t1>mbt,\ n=0} \times P_{t2>mbt,\ n=0} \times P_{total<=mtbt} \times P_{drip,\ n=0})$$

where $P_{t1>mbt,\ n=0}$ is the probability that no first burn time exceeds a maximum burn time value, $P_{t2>mbt,\ n=0}$ is the probability that no second burn time exceeds a maximum burn time value, $P_{total<=mtbt}$ is the probability that the sum of the burn times is less than or equal to a maximum total burn time value, and $P_{drip,\ n=0}$ is the probability that no specimen exhibits dripping during the flame test. First and second burn time refer to burn times after a first and second application of the flame, respectively.

The probability that no first burn time exceeds a maximum burn time value, $P_{t1>mbt,\ n=0}$, may be determined from the formula:

$$P_{t1>mbt,\ n=0} = (1 - P_{t1>mbt})^5$$

where $P_{t1>mbt}$ is the area under the log normal distribution curve for $_{t1>mbt}$.

and where the exponent "5" relates to the number of bars tested.

The probability that a single second burn time exceeds a maximum burn time value may be determined from the formula:

$$P_{t2>mbt,\ n=0} = (1 - P_{t2>mbt})^5$$

where $P_{t2>mbt}$ is the area under the normal distribution curve for $_{t2>mbt}$. As above, the mean and standard deviation of the burn time data set are used to calculate the normal distribution curve. For the UL-94 V-0 rating, the maximum burn time is 10 seconds. For a V-1 or V-2 rating the maximum burn time is 30 seconds.

The probability $P_{drip,\ n=0}$ that no specimen exhibits dripping during the flame test is an attribute function, estimated by:

$$(1 - P_{drip})^5$$

where $P_{drip}$ = the number of bars that drip/the number of bars tested.

The probability $P_{total<=mtbt}$ that the sum of the burn times is less than or equal to a maximum total burn time value may be determined from a normal distribution curve of simulated 5-bar total burn times. The distribution may be generated from a Monte Carlo simulation of 1000 sets of five bars using the distribution for the burn time data determined above. Techniques for Monte Carlo simulation are well known in the art. A normal distribution curve for 5-bar total burn times may be generated using the mean and standard deviation of the simulated 1000 sets. Therefore, $P_{total<=mtbt}$ may be determined from the area under a log normal distribution curve of a set of 1000 Monte Carlo simulated 5-bar total burn time for total<=maximum total burn time. For the UL-94 V-0 rating, the maximum total burn time is 50 seconds. For a V-1 or V-2 rating, the maximum total burn time is 250 seconds.

The probability of a retest is determined according to the following formula:

$$P_{retest} = (P_{t1>mbt,\ n=1} \times P_{t2>mbt,\ n=0} \times P_{total<=mtbt} \times P_{drip,\ n=0})$$

$$+ (P_{t1>mbt,\ n=0} \times P_{t2>mbt,\ n=1} \times P_{total<=mtbt} \times P_{drip,\ n=0})$$

$$+ (P_{t1>mbt,\ n=0} \times P_{t2>mbt,\ n=0} \times P_{mtbt<total<=mtbt} \times P_{drip,\ n=0})$$

$$+ (P_{t1>mbt,\ n=0} \times P_{t2>mbt,\ n=0} \times P_{total<=mtbt} \times P_{drip,\ n=1})$$

where $P_{t1>mbt,\ n=1}$ is the probability that a single first burn time exceeds a maximum burn time value, $P_{t2>mbt,\ n=1}$ is the probability that a single second burn time exceeds a maximum burn time value, $P_{mtbt<total<=mrtbt}$ is the probability that the sum of individual burn times is greater than the maximum total burn time value and is less than or equal to the maximum retest total burn time value, $P_{drip,\ n=1}$ is the probability that a single specimen exhibits dripping during the flame test and $P_{t1>mbt,\ n=0}$, $P_{t2>mbt,\ n=0}$, $P_{total<=mtbt}$, and $P_{drip,\ n=0}$, are as defined above.

The probability that a single first burn time exceeds a maximum burn time value may be determined from the formula:

$$P_{t1>mbt,\ n=1} = 5 \times P_{t1>mbt} \times (1 - P_{t1>mbt})^4$$

where $P_{t1>mbt}$ is defined as above.

The probability that a single second burn time exceeds a maximum burn time value may be determined from the formula:

$$P_{t2>mbt,\ n=1} = 5 \times P_{t2>mbt} \times (1 - P_{t2>mbt})^4$$

where $P_{t2>mbt}$ is defined above.

The probability that the sum of individual burn times is greater than the maximum total burn time value and is less than or equal to the maximum retest total burn time value may be determined from the normal distribution curve of simulated 5-bar total times, as described above for $P_{total<=mtbt}$. $P_{mtbt<total<=mrtbt}$ is equal to the area under a log normal distribution curve of a set of 1000 Monte Carlo simulated 5-bar total burn time for maximum total burn time<total<=the maximum retest total burn time value. For the UL-94 V-0 rating, the maximum total burn time is 50 seconds, and the maximum retest total burn time value is 55 seconds. For a V-1 or V-2 rating, the maximum total burn time is 250 seconds, and the maximum retest total burn time value is 255.

The probability that a single specimen exhibits dripping during the flame test may be estimated from the following attribute function:

$$P_{drip,\ n=1} = 5 \times P_{drip} \times (1-P_{drip})^4$$

where $P_{drip}$ is defined as for a first time pass, above.

By definition, the sum of the probabilities of possible outcomes of a first submittal is one:

$$\text{E Probabilities} = P_{first\ time\ pass} + P_{retest} + P_{failure,\ no\ retest} = 1.$$

Therefore, the probability of a failure is given by:

$$P_{failure,\ no\ retest} = 1 - P_{first\ time\ pass} - P_{retest}$$

The probability of a first submittal pass is given by:

$$P_{1st\ submittal\ pass} = P_{first\ time\ pass} + P_{retest} \times P_{first\ time\ pass}$$

where $P_{first\ time\ pass}$ and $P_{retest}$ are as defined above.

The probability of a second submittal pass is determined according to:

$$P_{2nd\ submittal\ pass} = P_{failure,\ no\ retest} \times (P_{first\ time\ pass} + P_{retest} \times P_{first\ time\ pass})$$

where $P_{first\ time\ pass}$, $P_{retest}$ and $P_{failure}$, no retest as defined above.

Finally, the probability of a pass after a first and second submittal, or the overall probability of a pass is:

$$P_{overall\ pass} = P_{1st\ submittal\ pass} + P_{2nd\ submittal\ pass}$$

In one embodiment, statistical analysis of data obtained from flame testing of a polymer composition according to the method of the present invention is performed by a computing system. One example of a computing environment for performing the statistical analysis method of the present invention and the techniques associated therewith is depicted in FIG. 4 and described in detail below.

Figure 4:
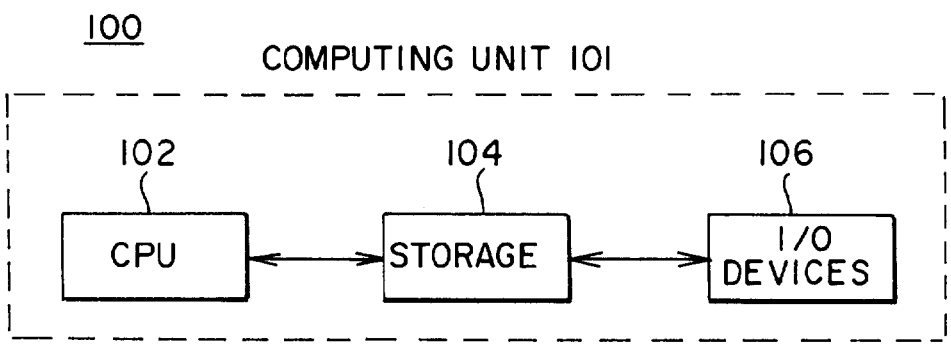
FIG. 4 depicts an example of a computer system incorporating and using the method of the present invention.

Referring to FIG. 4, a computing environment 100 includes, for instance, a computing unit 101 having at least one central processing unit 102, a main storage 104 and one or more input/output devices 106, each of which is described below.

As is known, central processing unit (CPU) 102 is the controlling center of computing unit 101 and provides the sequencing and processing facilities for instruction execution, interruption action, timing functions, initial program loading and other machine related functions. The central processing unit executes at least one operating system, which as is known, is used to control the operation of the computing unit by controlling the execution of other programs, controlling communication with peripheral devices and controlling use of the computer resources.

Central processing unit 102 is coupled to main storage 104, which is directly accessible and provides for high-speed processing of data by the central processing unit. Main storage 104 may be either physically integrated with the CPU, or constructed in stand-alone units.

Main storage 104 is also coupled to one or more input/output devices 106. These devices include, for instance, keyboards, communications controllers, teleprocessing devices, printers, magnetic storage media (e.g., tapes, disks), direct access storage devices, and sensor based equipment. Data is transferred from main storage 104 to input/output devices 106 and from the input/output devices back to main storage.

In one example, computing environment 100 includes a personal computer running a Windows® operating system, which is offered by Microsoft Corporation. As another example, computing environment 100 includes an RS/6000 computer system running an AIX operating system, which are also offered by International Business Machines Corporation. The invention is not limited to such environments, however. The capabilities of the present invention can be incorporated and used with many types of computer environments and with many types of computer systems or platforms. The above systems are only offered as examples.

The present invention may be included in an article of manufacture (e.g., one or more computer program products) having, for instance, computer usable media. The media have embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

What is claimed is:

1. A method for determining flame retardance of polymer compositions, said method comprising:
   subjecting a plurality of specimens of a polymer composition to a flame test, wherein data is obtained from said flame test; and
   performing a statistical analysis of the data, said statistical analysis comprising using said data to determine a probability of at least one possible outcome of said flame test, wherein said probability of said at least one possible outcome provides a measure of the flame retardance of the polymer composition.

2. The method of claim 1, wherein said flame test is a UL-94 flame test.

3. The method of claim 1, wherein said plurality of specimens is at least twenty specimens.

4. The method of claim 1, wherein said using said data comprises converting the data to equivalent logarithmic values and using the equivalent logarithmic values to determine the probability of said at least one possible outcome.

5. The method of claim 1, wherein said at least one possible outcome comprises one or more of a first time pass, a retest, a first submittal pass, a second submittal pass, and a failure.

6. The method of claim 5, wherein said at least one possible outcome is a first time pass, and said data comprises one or more burn times of said plurality of specimens resulting from said flame test, and wherein said using said data comprises determining said probability of said first time pass according to:

$$P_{first\ time\ pass} = (P_{t1>mbt,\ n=0} \times P_{t2>mbt,\ n=0} \times P_{total<=mtbt} \times P_{drip,\ n=0})$$

where $P_{t1>mbt,\ n=0}$ is a probability that no first burn time exceeds a maximum burn time value, $P_{t2>mbt,\ n=0}$ is a probability that no second burn time exceeds a maximum burn time value, $P_{total<=mtbt}$ is a probability that a sum of the burn times is less than or equal to a maximum total burn time value, and $P_{drip,\ n=0}$ is a probability that no specimen of said plurality of specimens exhibits dripping during said flame test.

7. The method of claim 5, wherein said at least one possible outcome is a retest, and said data comprises one or more burn times of said plurality of specimens resulting from said flame test, and wherein said using said data comprises determining said probability of said retest according to:

$$P_{retest}=(P_{t1>mbt,\ n=1} \times P_{t2>mbt,\ n=0} \times P_{total<=mtbt} \times P_{drip,\ n=0})$$
$$+(P_{t1>mbt,\ n=0} \times P_{t2>mbt,\ n=1} \times P_{total<=mtbt} \times P_{drip,\ n=0})$$
$$+(P_{t1>mbt,\ n=0} \times P_{t2>mbt,\ n=0} \times P_{mtbt<total<=mrtbt} \times P_{drip,\ n=0})$$
$$+(P_{t1>mbt,\ n=0} \times P_{t2>mbt,\ n=0} \times P_{total<=mtbt} \times P_{drip,\ n=1})$$

where $P_{t1>mbt,\ n=1}$ is the probability that a single first burn time exceeds a maximum burn time value, $P_{t2>mbt,\ n=1}$ is the probability that a single second burn time exceeds a maximum burn time value, $P_{mtbt<total<=mrtbt}$ is the probability that the sum of individual burn times is greater than the maximum total burn time value and is less than or equal to the maximum retest total burn time value, $P_{drip,\ n=1}$ is the probability that a single specimen exhibits dripping during the flame test, $P_{t1>mbt,\ n=0}$ is a probability that no first burn time exceeds a maximum burn time value, $P_{t2>mbt,\ n=0}$ is a probability that no second burn time exceeds a maximum burn time value, $P_{total<=mtbt}$ is a probability that a sum of the burn times is less than or equal to a maximum total burn time value, and $P_{drip,\ n=0}$ is a probability that no specimen of said plurality of specimens exhibits dripping during said flame test.

8. The method of claim 5, wherein said at least one possible outcome is a failure, and said data comprises one or more burn times of said plurality of specimens resulting from said flame test, and wherein said using said data comprises determining said probability of said failure according to:

$$P_{failure,\ no\ retest}=1-P_{first\ time\ pass}-P_{retest}$$

where $P_{first\ time\ pass}$ is the probability of a first time pass and $P_{retest}$ is the probability of a retest.

9. The method of claim 5, wherein said at least one possible outcome is a first submittal pass, and said data comprises one or more burn times of said plurality of specimens resulting from said flame test, and wherein said using said data comprises determining said probability of said first submittal pass according to:

$$P_{1st\ submittal\ pass}=P_{first\ time\ pass}+P_{retest} \times P_{first\ time\ pass}$$

where $P_{first\ time\ pass}$ is the probability of a first time pass and $P_{retest}$ is the probability of a retest.

10. The method of claim 5, wherein said at least one possible outcome is a second submittal pass and a probability of said second submittal pass is determined according to:

$$P_{2nd\ submittal\ pass}=P_{failure,\ no\ retest} \times (P_{first\ time\ pass}+P_{retest} \times P_{first\ time\ pass})$$

where $P_{first\ time\ pass}$ is the probability of a first time pass, $P_{retest}$ is the probability of a retest and $P_{failure,\ no\ retest}$ is the probability of a failure.

11. A system for determining flame retardance of a polymer composition, said system comprising:
 means for obtaining data resulting from subjecting a plurality of specimens of a polymer composition to a flame test; and
 means for performing statistical analysis of said data, said means for performing statistical analysis comprising means for using said data to determine a probability of at least one possible outcome of said flame test, wherein said probability of said at least one possible outcome provides a measure of the flame retardance of the polymer composition.

12. The system of claim 11, wherein said flame test is a UL-94 flame test.

13. The system of claim 11, wherein said plurality of specimens is at least twenty specimens.

14. The system of claim 11, wherein said using said data comprises converting the data to equivalent logarithmic values and using the equivalent logarithmic values to determine the probability of said at least one possible outcome.

15. The system of claim 11, wherein said at least one possible outcome comprises one or more of a first time pass, a retest, a first submittal pass, a second submittal pass, and a failure.

16. The system of claim 15, wherein said at least one possible outcome is a first time pass, and said data comprises one or more burn times of said plurality of specimens resulting from said flame test, and wherein said using said data comprises determining said probability of said first time pass according to:

$$P_{first\ time\ pass}=(P_{t1>mbt,\ n=0} \times P_{t2>mbt,\ n=0} \times P_{total<=mtbt} \times P_{drip,\ n=0})$$

where $P_{t1>mbt,\ n=0}$ is a probability that no first burn time exceeds a maximum burn time value, $P_{t2>mbt,\ n=0}$ is a probability that no second burn time exceeds a maximum burn time value, $P_{total<=mtbt}$ is a probability that a sum of the burn times is less than or equal to a maximum total burn time value, and $P_{drip,\ n=0}$ is a probability that no specimen of said plurality of specimens exhibits dripping during said flame test.

17. The system of claim 15, wherein said at least one possible outcome is a retest, and said data comprises one or more burn times of said plurality of specimens resulting from said flame test, and wherein said using said data comprises determining said probability of said retest according to:

$$P_{retest}=(P_{t1>mbt,\ n=1} \times P_{t2>mbt,\ n=0} \times P_{total<=mtbt} \times P_{drip,\ n=0})$$
$$+(P_{t1>mbt,\ n=0} \times P_{t2>mbt,\ n=1} \times P_{total<=mtbt} \times P_{drip,\ n=0})$$
$$+(P_{t1>mbt,\ n=0} \times P_{t2>mbt,\ n=0} \times P_{mtbt<total<=mrtbt} \times P_{drip,\ n=0})$$
$$+(P_{t1>mbt,\ n=0} \times P_{t2>mbt,\ n=0} \times P_{total<=mtbt} \times P_{drip,\ n=1})$$

where $P_{t1>mbt,\ n=1}$ is the probability that a single first burn time exceeds a maximum burn time value, $P_{t2>mbt,\ n=1}$ is the probability that a single second burn time exceeds a maximum burn time value, $P_{mtbt<total<=mrtbt}$ is the probability that the sum of individual burn times is greater than the maximum total burn time value and is less than or equal to the maximum retest total burn time value, $P_{drip,\ n=1}$ is the probability that a single specimen exhibits dripping during the flame test, $P_{t1>mbt,\ n=0}$ is a probability that no first burn time exceeds a maximum burn time value, $P_{t2>mbt,\ n=0}$ is a probability that no second burn time exceeds a maximum burn time value, $P_{total<=mtbt}$ is a probability that a sum of the burn times is less than or equal to a maximum total burn time value, and $P_{drip,\ n=0}$ is a probability that no specimen of said plurality of specimens exhibits dripping during said flame test.

18. The system of claim 15, wherein said at least one possible outcome is a failure, and said data comprises one or more burn times of said plurality of specimens resulting from said flame test, and wherein said using said data comprises determining said probability of said failure according to:

$$P_{failure,\ no\ retest} = 1 - P_{first\ time\ pass} - P_{retest}$$

where $P_{first\ time\ pass}$ is the probability of a first time pass and $P_{retest}$ is the probability of a retest.

19. The system of claim 15, wherein said at least one possible outcome is a first submittal pass, and said data comprises one or more burn times of said plurality of specimens resulting from said flame test, and wherein said using said data comprises determining said probability of said first submittal pass according to:

$$P_{1st\ submittal\ pass} = P_{first\ time\ pass} + P_{retest} \times P_{first\ time\ pass}$$

where $P_{first\ time\ pass}$ is the probability of a first time pass and $P_{retest}$ is the probability of a retest.

20. The system of claim 15, wherein said at least one possible outcome is a second submittal pass and a probability of said second submittal pass is determined according to:

$$P_{2nd\ submittal\ pass} = P_{failure,\ no\ retest} \times (P_{first\ time\ pass} + P_{retest} \times P_{first\ time\ pass})$$

where $P_{first\ time\ pass}$ is the probability of a first time pass, $P_{retest}$ is the probability of a retest and $P_{failure,\ no\ retest}$ is the probability of a failure.

21. An article of manufacture comprising:
at least one computer usable medium having computer readable program code means embodied therein for causing a determination of flame retardance of polymer compositions, the computer readable program code means in said article of manufacture comprising:
a first computer readable program code segment for causing a computer to obtain data resulting from subjecting a plurality of specimens of a polymer composition to a flame test; and
a second computer readable program code segment for causing a computer to perform a statistical analysis of the data, said statistical analysis comprising using said data to determine a probability of at least one possible outcome of the flame test, wherein said probability of said at least one possible outcome provides a measure of the flame retardance of the polymer.

22. The article of claim 21, wherein said flame test is a UL-94 flame test.

23. The article of claim 21, wherein said plurality of specimens is at least twenty specimens.

24. The article of claim 21, wherein said using said data comprises converting the data to equivalent logarithmic values and using the equivalent logarithmic values to determine the probability of said at least one possible outcome.

25. The article of claim 21, wherein said at least one possible outcome comprises one or more of a first time pass, a retest, a first submittal pass, a second submittal pass, and a failure.

26. The article of claim 25, wherein said at least one possible outcome is a first time pass, and said data comprises one or more burn times of said plurality of specimens resulting from said flame test, and wherein said using said data comprises determining said probability of said first time pass according to:

$$P_{first\ time\ pass}\ (P_{t1>mbt,\ n=0} \times P_{t2>mbt,\ n=0} \times P_{total<=mtbt} \times P_{drip,\ n=0})$$

where $P_{t1>mbt,\ n=0}$ is a probability that no first burn time exceeds a maximum burn time value, $P_{t2>mbt,\ n=0}$ is a probability that no second burn time exceeds a maximum burn time value, $P_{total<=mtbt}$ is a probability that a sum of the burn times is less than or equal to a maximum total burn time value, and $P_{drip,\ n=0}$ is a probability that no specimen of said plurality of specimens exhibits dripping during said flame test.

27. The article of claim 25, wherein said at least one possible outcome is a retest, and said data comprises one or more burn times of said plurality of specimens resulting from said flame test, and wherein said using said data comprises determining said probability of said retest according to:

$$P_{retest} = (P_{t1>mbt,\ n=1} \times P_{t2>mbt,\ n=0} \times P_{total<=mtbt} \times P_{drip,\ n=0})$$

$$+ (P_{t1>mbt,\ n=0} \times P_{t2>mbt,\ n=1} \times P_{total<=mtbt} \times P_{drip,\ n=0})$$

$$+ (P_{t1>mbt,\ n=0} \times P_{t2>mbt,\ n=0} \times P_{mtbt<total<=mrtbt} \times P_{drip,\ n=0})$$

$$+ (P_{t1>mbt,\ n=0} \times P_{t2>mbt,\ n=0} \times P_{total<=mtbt} \times P_{drip,\ n=1})$$

where $P_{t1>mbt,\ n=1}$ is the probability that a single first burn time exceeds a maximum burn time value, $P_{t2>mbt,\ n=1}$ is the probability that a single second burn time exceeds a maximum burn time value, $P_{mtrbt<total<=mtbt}$ is the probability that the sum of individual burn times is greater than the maximum total burn time value and is less than or equal to the maximum retest total burn time value, $P_{drip,\ n=1}$ is the probability that a single specimen exhibits dripping during the flame test, $P_{t1>mbt,\ n=0}$ is a probability that no first burn time exceeds a maximum burn time value, $P_{t2>mbt,\ n=0}$ is a probability that no second burn time exceeds a maximum burn time value, $P_{total<=mtbt}$ is a probability that a sum of the burn times is less than or equal to a maximum total burn time value, and $P_{drip,\ n=0}$ is a probability that no specimen of said plurality of specimens exhibits dripping during said flame test.

28. The article of claim 25, wherein said at least one possible outcome is a failure, and said data comprises one or more burn times of said plurality of specimens resulting from said flame test, and wherein said using said data comprises determining said probability of said failure according to:

$$P_{failure,\ no\ retest} = 1 - P_{first\ time\ pass} - P_{retest}$$

where $P_{first\ time\ pass}$ is the probability of a first time pass and $P_{retest}$ is the probability of a retest.

29. The article of claim 25, wherein said at least one possible outcome is a first submittal pass, and said data comprises one or more burn times of said plurality of specimens resulting from said flame test, and wherein said using said data comprises determining said probability of said first submittal pass according to:

$$P_{1st\ submittal\ pass} = P_{first\ time\ pass} + P_{retest} \times P_{first\ time\ pass}$$

where $P_{first\ time\ pass}$ is the probability of a first time pass and $P_{retest}$ is the probability of a retest.

30. The article of claim 25, wherein said at least one possible outcome is a second submittal pass and a probability of said second submittal pass is determined according to:

$$P_{2nd\ submittal\ pass} = P_{failure,\ no\ retest} \times (P_{first\ time\ pass} + P_{retest} \times P_{first\ time\ pass})$$

where $P_{first\ time\ pass}$ is the probability of a first time pass, $P_{retest}$ is the probability of a retest and $P_{failure,\ no\ retest}$ is the probability of a failure.

* * * * *

UNITED STATES PATENT AND TRADEMARK OFFICE
CERTIFICATE OF CORRECTION

PATENT NO. : 6,308,142 B1
DATED : October 23, 2001
INVENTOR(S) : Choate et al.

It is certified that error appears in the above-identified patent and that said Letters Patent is hereby corrected as shown below:

Column 6,
Line 1, delete "a single" and substitute therefor -- no --.

Signed and Sealed this

Fifteenth Day of March, 2005

JON W. DUDAS
*Director of the United States Patent and Trademark Office*